United States Patent
Ishii et al.

(10) Patent No.: US 10,478,073 B2
(45) Date of Patent: Nov. 19, 2019

(54) MEDICAL IMAGE PROCESSING APPARATUS

(71) Applicant: Toshiba Medical Systems Corporation, Otawara-shi (JP)

(72) Inventors: Hideaki Ishii, Nasushiobara (JP); Satoshi Wakai, Nasushiobara (JP); Kazumasa Arakita, Nasushiobara (JP); Takuma Igarashi, Nasushiobara (JP); Yasuko Fujisawa, Nasushiobara (JP); Shigeo Kaminaga, Otawara (JP); Kenji Hirohata, Tokyo (JP); Junichiro Ooga, Tokyo (JP)

(73) Assignee: Canon Medical Systems Corporation, Otawara-shi (JP)

( * ) Notice: Subject to any disclaimer, the term of this patent is extended or adjusted under 35 U.S.C. 154(b) by 477 days.

(21) Appl. No.: 14/725,893

(22) Filed: May 29, 2015

(65) Prior Publication Data

US 2015/0257655 A1    Sep. 17, 2015

Related U.S. Application Data

(63) Continuation of application No. PCT/JP2013/082220, filed on Nov. 29, 2013.

(30) Foreign Application Priority Data

Nov. 30, 2012  (JP) ................................. 2012-263567

(51) Int. Cl.
*A61B 5/02*  (2006.01)
*A61B 5/026*  (2006.01)
(Continued)

(52) U.S. Cl.
CPC .......... *A61B 5/02007* (2013.01); *A61B 6/032* (2013.01); *A61B 6/486* (2013.01);
(Continued)

(58) Field of Classification Search
CPC ..... A61B 5/02007; A61B 6/032; A61B 6/486; A61B 6/503; A61B 6/504; A61B 6/5217;
(Continued)

(56) References Cited

U.S. PATENT DOCUMENTS

| | | | | |
|---|---|---|---|---|
| 5,859,922 A | * | 1/1999 | Hoffmann | A61B 6/584 382/128 |
| 2006/0036167 A1 | * | 2/2006 | Shina | A61B 6/12 600/433 |

(Continued)

FOREIGN PATENT DOCUMENTS

| | | |
|---|---|---|
| JP | 2004-081866 A | 3/2004 |
| JP | 2007-508096 A | 4/2007 |

(Continued)

OTHER PUBLICATIONS

International Search Report dated Jan. 28, 2014 for PCT/JP2013/082220 filed Nov. 29, 2013 with English Translation.

(Continued)

*Primary Examiner* — Carl H Layno
*Assistant Examiner* — Erin M Piateski
(74) *Attorney, Agent, or Firm* — Oblon, McClelland, Maier & Neustadt, L.L.P.

(57) ABSTRACT

A centerline extraction unit extracts at least two coronary artery centerline structures from at least two images respectively corresponding to at least two cardiac phases concerning a heart, an interpolation processing unit interpolates coronary artery centerline structures concerning other cardiac phases from the at least two extracted coronary artery centerline structures to generate coronary artery centerline structures respectively corresponding to a plurality of cardiac phases throughout one heartbeat of the heart, and a displacement distribution calculation unit calculates a plurality of displacement distributions between the respective (Continued)

cardiac phases from a plurality of coronary artery centerline structures throughout the one heartbeat.

16 Claims, 8 Drawing Sheets

(51) Int. Cl.
    *A61B 6/03*     (2006.01)
    *A61B 6/00*     (2006.01)
    *G06T 7/13*     (2017.01)

(52) U.S. Cl.
    CPC .............. *A61B 6/503* (2013.01); *A61B 6/504* (2013.01); *A61B 6/5217* (2013.01); *G06T 7/13* (2017.01); *A61B 5/026* (2013.01); *A61B 5/02028* (2013.01); *A61B 2576/023* (2013.01); *G06T 2207/10081* (2013.01); *G06T 2207/30101* (2013.01); *G06T 2207/30172* (2013.01)

(58) Field of Classification Search
    CPC ............... A61B 5/02028; A61B 5/026; A61B 2576/023; G06T 7/13; G06T 2207/10081; G06T 2207/30101; G06T 2207/30172
    USPC ........................................................ 600/508
    See application file for complete search history.

(56) References Cited

U.S. PATENT DOCUMENTS

| | | | |
|---|---|---|---|
| 2007/0073142 A1 | 3/2007 | Eck et al. | |
| 2011/0075896 A1* | 3/2011 | Matsumoto | G06T 3/4007 382/128 |
| 2012/0020452 A1* | 1/2012 | Arakita | A61B 6/03 378/8 |
| 2012/0041318 A1* | 2/2012 | Taylor | A61B 5/02007 600/504 |
| 2012/0063663 A1 | 3/2012 | Kawasaki | |
| 2012/0078097 A1* | 3/2012 | Wang | G06T 7/251 600/437 |
| 2013/0094745 A1* | 4/2013 | Sundar | G06T 3/0068 382/132 |
| 2013/0101187 A1* | 4/2013 | Sundar | G06K 9/00362 382/128 |

FOREIGN PATENT DOCUMENTS

| | | |
|---|---|---|
| JP | 2007-151881 A | 6/2007 |
| JP | 2012-081254 A | 4/2012 |
| JP | 2014-108198 A | 6/2014 |
| JP | 2014-108199 A | 6/2014 |
| JP | 2014-113264 A | 6/2014 |
| JP | 2014-128650 A | 7/2014 |
| JP | 2014-128651 A | 7/2014 |

OTHER PUBLICATIONS

International Written Opinion dated Jan. 28, 2014 for PCT/JP2013/082220 filed Nov. 29, 2013.

James K. Min et al., "Rationale and Design of the DeFACTO (Determination of Fractional Flow Reserve by Anatomic Computed Tomographic AngiOgraphy) Study", Journal of Cardiovascular Computed Tomography, vol. 5, Issue 5, pp. 301-309, 2011.

* cited by examiner

MEDICAL IMAGE PROCESSING APPARATUS

CROSS-REFERENCE TO RELATED APPLICATIONS

This application is a Continuation application of PCT Application No. PCT/JP2013/082220, filed Nov. 29, 2013 and based upon and claims the benefit of priority from the Japanese Patent Application No. 2012-263567, filed Nov. 30, 2012, the entire contents of all of which are incorporated herein by reference.

FIELD

Embodiments described herein relate generally to a medical image processing apparatus.

BACKGROUND

As is known, an ischemic heart disease is a disorder in the heart which is caused when the flow of blood to the cardiac muscle becomes insufficient or is stopped by being blocked by occlusion, constriction, or the like of a coronary artery. The symptoms of this disease include pain and a feeling of tightness mainly in the precordium and sometimes in the left arm or back.

Figure 9:
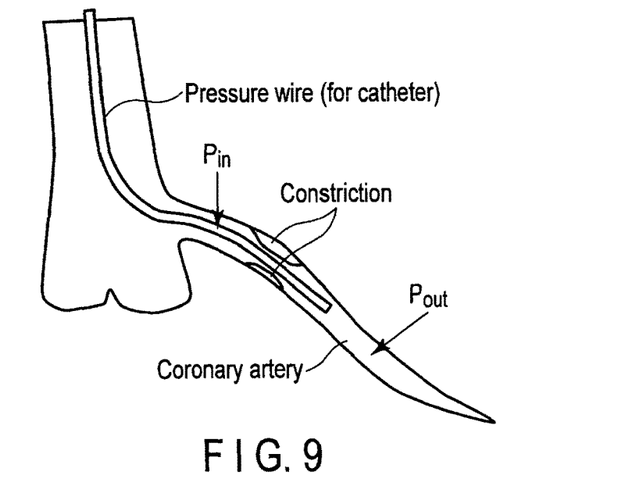
FIG. 9 is a supplementary view for explaining an FFR.

An FFR (Fractional Flow Reserve) is an index for determining whether the cardiac muscle is in an ischemic state due to a coronary stenosis. As shown in FIG. 9, a pressure wire is inserted into a blood vessel of an object to measure an upstream pressure Pin and a downstream pressure Pout of a constricted portion. The above index is defined as FFR=Pout/Pin.

In general, if the FFR value is less than 0.8 (serious condition), the patient requires a surgical treatment (PCI: Percutaneous Coronary Intervention), whereas if the FFR value is more than 0.8, the doctor often chooses a medicinal treatment. Since FFR measurement using a pressure wire is invasive, demands have arisen for non-invasive measurement/calculation methods.

Under the circumstances, a simulation-based measurement method using fluid analysis has recently been proposed.

This simulation is a three-dimensional simulation. The basic concept of simulation-based measurement is that an FFR is obtained by calculating a pressure using the Navier-Stokes equations, which are generally used in CFD (Computational Fluid Dynamics), using as inputs physical parameters such as the hardness of a blood vessel wall and the blood inflow rate calculated from contrast images.

Simulation-based measurement, however, requires time-series volume data throughout at least one heartbeat, and hence it takes much labor and time to perform imaging and data analysis. In addition, in a cardiac phase in which the heart moves fast, an image of a coronary artery sometimes blurs. There is therefore a possibility that data may contain an error.

DETAILED DESCRIPTION

A medical image processing apparatus according to this embodiment processes images in a plurality of cardiac phases concerning the heart. The apparatus extracts a plurality of coronary artery centerline structures from a plurality of images. The apparatus generates a plurality of coronary artery centerline structures throughout one heartbeat of the heart by interpolating coronary artery centerline structures concerning other cardiac phases from the plurality of extracted coronary artery centerline structures. The apparatus calculates a displacement distribution between the respective cardiac phases from the plurality of coronary artery centerline structures throughout one heartbeat. The apparatus generates a coronary artery model from an image concerning a specific phase. The apparatus deforms the coronary artery model for each cardiac phase based on the displacement distribution.

Figure 1:
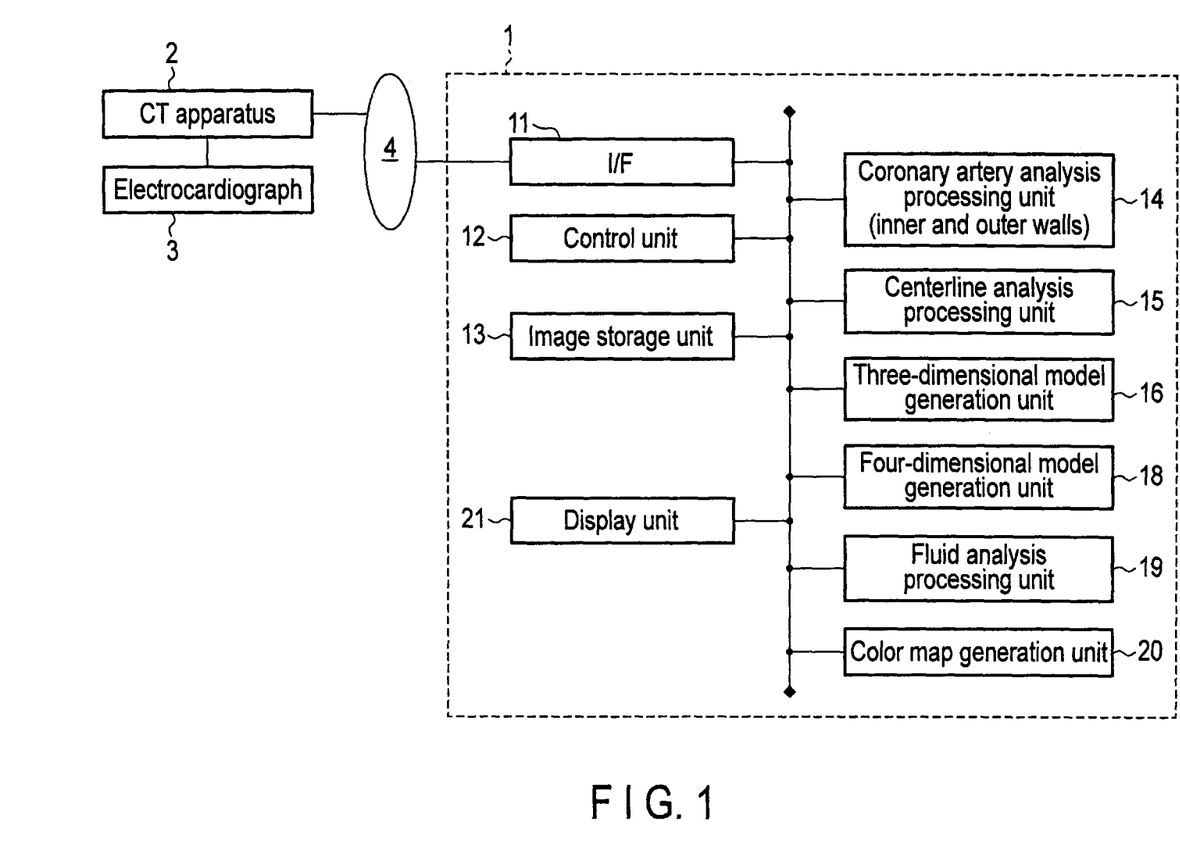
FIG. 1 is a block diagram showing the arrangement of a medical image processing apparatus according to an embodiment.

FIG. 1 shows the arrangement of the medical image processing apparatus according to this embodiment. A medical image processing apparatus 1 according to the embodiment is connected to a CT apparatus 2 including an electrocardiograph 3 via a network 4 such as a LAN or public electronic communication line. The CT apparatus 2 includes a two-dimensional array detector and implements volume scanning. The CT apparatus 2 generates three-dimensional CT image data (to be simply referred to as volume data hereinafter) by volume scanning.

The medical image processing apparatus 1 includes an interface 11. The medical image processing apparatus 1 includes an image storage unit 13 which stores volume data supplied from the CT apparatus 2 under the control of a control unit 12 and respectively corresponding to a plurality of cardiac phases concerning a chest region including the heart of the object as a processing target image. Each volume data is associated with a cardiac phase at the time of data acquisition, which is measured by the electrocardiograph 3. Note that a cardiac phase expresses each position in one heartbeat period by percentage.

A coronary artery analysis processing unit 14 extracts regions of the inner and outer walls of a coronary artery by using the coronary artery region extracted from volume data based on contrast medium CT values. A three-dimensional model generation unit 16 generates a three-dimensional coronary artery model indicating a stereoscopic structure constituted by inner wall lines and outer wall lines from the regions of the inner and outer walls extracted by the coronary artery analysis processing unit 14 and corresponding to a specific cardiac phase. Note that a specific cardiac phase is typically an end diastole (ED) in which pulsation is relatively small.

A centerline analysis processing unit 15 extracts a coronary artery centerline structure (wire model) indicating the centerlines of a coronary artery region extracted, based on contract medium CT values, from volume data respectively corresponding to two specific cardiac phases selected from the volume data respectively corresponding to a plurality of cardiac phases stored in the image storage unit 13 under the readout control of the control unit 12. Note that the two specific cardiac phases are typically an end systole (ES) and an end diastole (ED) in which pulsation is relatively small. The centerline analysis processing unit 15 generates coronary artery centerline structures in other cardiac phases from a coronary artery centerline structure in the end systole (ES) and a coronary artery centerline structure in the end diastole (ED) by interpolation processing. This generates a plurality of coronary artery centerline structures respectively corresponding to a plurality of cardiac phases throughout one heartbeat period. In addition, the centerline analysis processing unit 15 calculates a displacement at each point on a centerline between the respective cardiac phases, i.e., a moving direction and a moving distance, from a plurality of coronary artery centerline structures respectively corresponding to a plurality of cardiac phases throughout one heartbeat period, and generates a corresponding displacement distribution.

A four-dimensional model generation unit 18 deforms the three-dimensional coronary artery model in accordance with the displacement distribution. The four-dimensional model generation unit 18 generates a plurality of three-dimensional coronary artery models respectively corresponding to a plurality of cardiac phases throughout one heartbeat period by linking deformation processes in all the cardiac phases. Such a plurality of three-dimensional coronary artery models constituting time-series data will be collectively referred to as a four-dimensional coronary artery deformation model.

A fluid analysis processing unit 19 calculates displacement amounts (e.g., a diameter change, bending angle change, and moving distance) of the coronary artery between the respective cardiac phases at each position on the coronary artery from the four-dimensional coronary artery deformation model, and calculates the hardness of the blood vessel wall and a blood inflow rate from the deformation amount for each position and each cardiac phase. The fluid analysis processing unit 19 also calculates a pressure for each position on the coronary artery and each cardiac phase by applying fluid analysis processing to the hardness of the blood vessel wall and the distribution of blood inflow rates. This can generate a pressure distribution approximated to the actual measurement by a pressure wire.

A color map generation unit 20 converts the pressure distributions in the respective cardiac phases into color maps with different hues corresponding to the pressures by using a predetermined lookup table. A display unit 21 superimposes and displays each color map on the three-dimensional coronary artery model in a corresponding cardiac phase.

Figure 2:
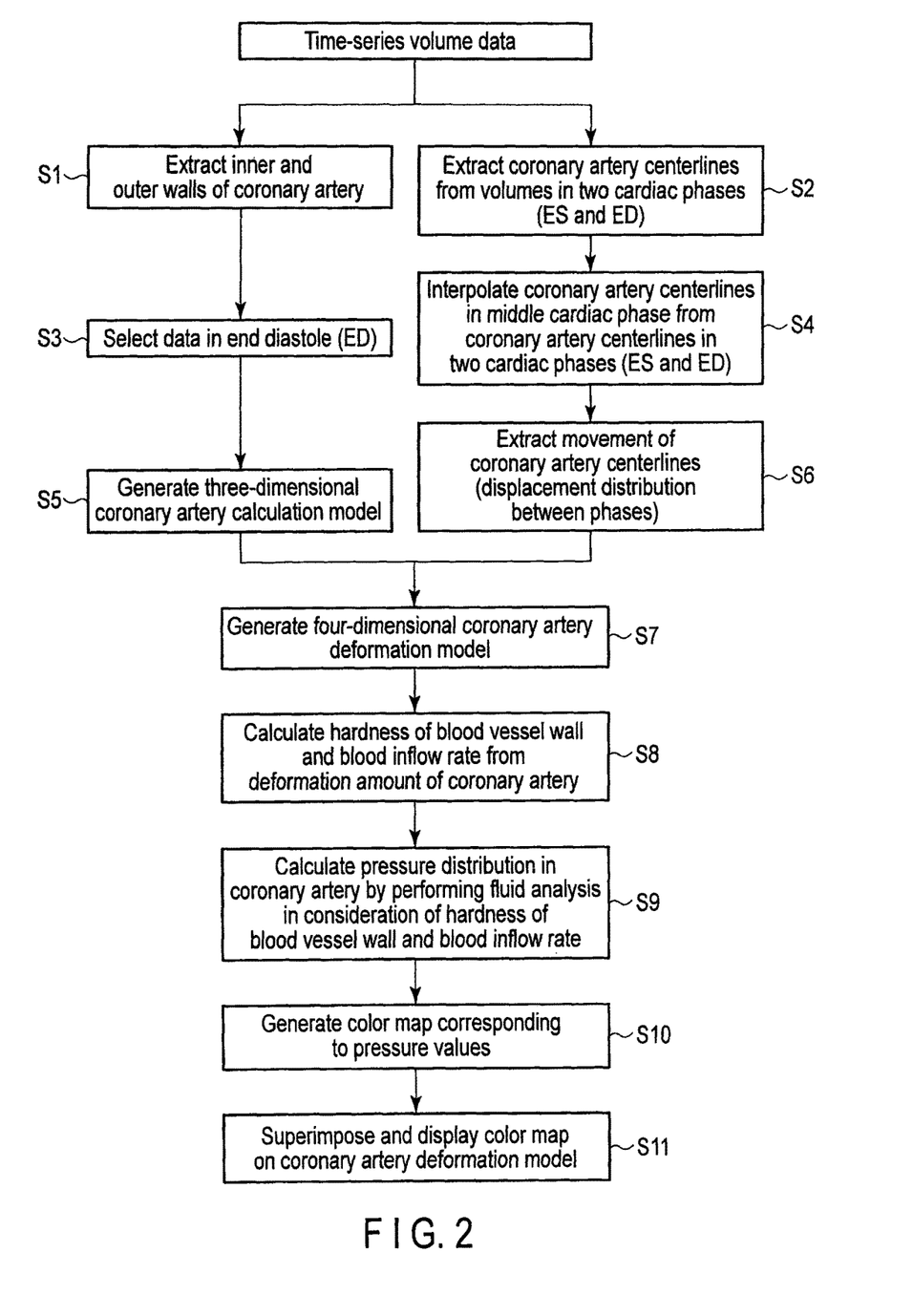
FIG. 2 is a flowchart showing a procedure for medical image processing according to this embodiment.
Figure 4:
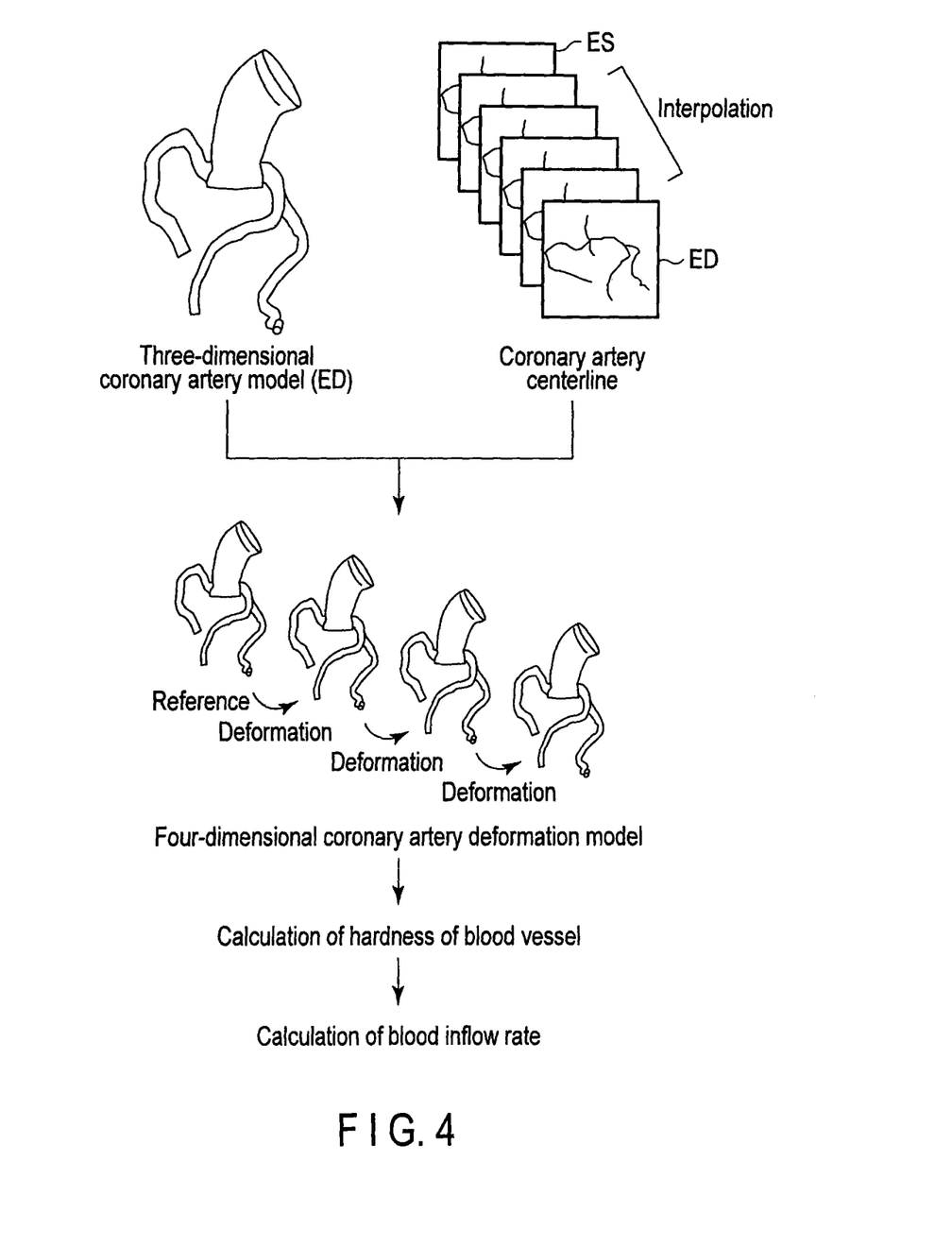
FIG. 4 is a view showing a concept of steps S5, S4, and S7 in FIG. 2.

FIG. 2 shows a procedure for medical image processing according to this embodiment. The coronary artery analysis processing unit 14 extracts a coronary artery region (contrast medium region) based on the CT value of the contrast medium from each time-series volume data stored in the image storage unit 13, and extracts the inner and outer walls of the coronary artery from the coronary artery region (S1). The apparatus then selects the data of the inner and outer walls in a specific cardiac phase from, typically a cardiac phase in end diastole in which pulsation is small, from the inner and outer walls in the respective cardiac phases under the readout control of the control unit 12 (S3). The three-dimensional model generation unit 16 generates three-dimensional coronary artery model (see the upper left of FIG. 4) indicating the stereoscopic structure of coronary artery blood vessels corresponding to the end diastole phase from the data of the inner and outer walls in the end diastole phase (S5).

Figure 3:
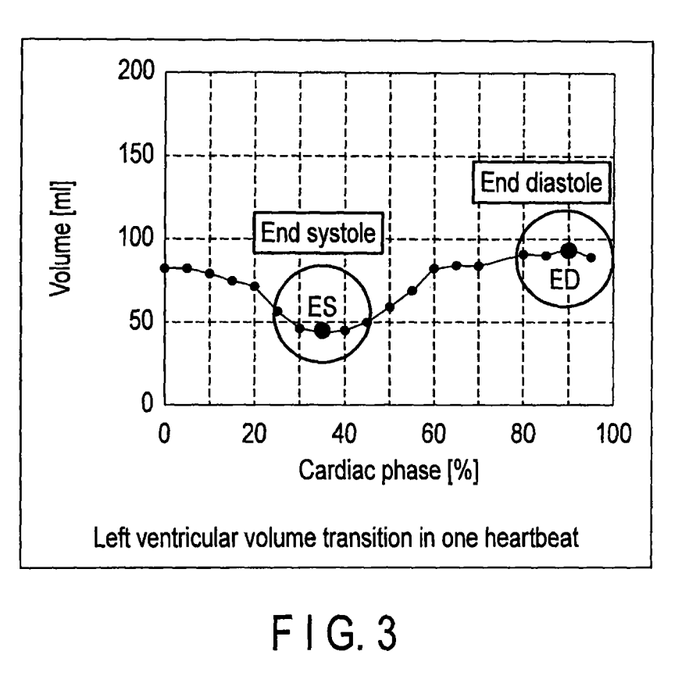
FIG. 3 is a graph showing two cardiac phases (ES and ED) in step S2 in FIG. 2.

The centerline analysis processing unit 15 extracts coronary artery centerline structures (see upper right of FIG. 4) indicating centerlines in the coronary artery region extracted, based on the CT value of the contrast medium, for volume data selected from volume data respectively corresponding to a plurality of cardiac phases stored in the image storage unit 13 under the readout control of the control unit 12, typically volume data respectively corresponding to two cardiac phases, i.e., an end systole (ES) and an end diastole (ED) in which pulsation is relatively small (S2), as shown in FIG. 3. The centerline analysis processing unit 15 generates a plurality of coronary artery centerline structures respectively corresponding to a plurality of cardiac phases between the end systole (ES) and the end diastole (ED) from the coronary artery centerline structure in the end systole (ES) and the coronary artery centerline structure in the end diastole (ED) by interpolation processing (S4). This generates a plurality of coronary artery centerline structures respectively corresponding to a plurality of cardiac phases throughout one heartbeat period. The apparatus then calculates a displacement (a moving direction and moving distance) at each point on a centerline between the respective cardiac phases from the plurality of coronary artery centerline structures respectively corresponding to the plurality of cardiac phases throughout one heartbeat period (S6).

The four-dimensional model generation unit 18 generates a four-dimensional model by deforming the three-dimensional coronary artery model in the end diastole (ED) as a reference in a chained manner (see the middle of FIG. 4) in accordance with the displacement distributions in the respective cardiac phases (S7).

The fluid analysis processing unit 19 calculates displacement amounts (e.g., a diameter change, bending angle change, and moving distance) of the coronary artery between the respective cardiac phases, for each position on the coronary artery, from this four-dimensional coronary artery deformation model, and calculates the hardness of the blood vessel wall and the blood inflow rate from the displacement amounts for each position and each cardiac phase (S8). The fluid analysis processing unit 19 calculates a pressure distribution for each cardiac phase on the coronary artery by applying fluid analysis processing to the hardness of the blood vessel wall and the distribution of blood inflow rates (S9).

The color map generation unit 20 converts the pressure distributions in the respective cardiac phases into color maps with different hues corresponding to the pressures by using a predetermined lookup table (S10). A display unit 21 superimposes and displays each color map on the three-dimensional coronary artery model in a corresponding cardiac phase (S11).

As described above, the apparatus generates a plurality of three-dimensional coronary artery models, i.e., a four-dimensional coronary artery deformation model, concerning a plurality of cardiac phases throughout one heartbeat by interpolating centerline structures in cardiac phases, other than a specific cardiac phase which is important for the analysis of the movement of the coronary artery and in which the heart does not move much, with reference to the centerline structure in the specific cardiac phase, and deforming the three-dimensional coronary artery model in the specific cardiac phase, in which the heart does not move much, from the centerline structures. This can shorten the time required for imaging and data analysis. In addition, it is possible to prevent the occurrence of analysis errors by thinning out cardiac phases in which the heart moves fast.

Figure 5:
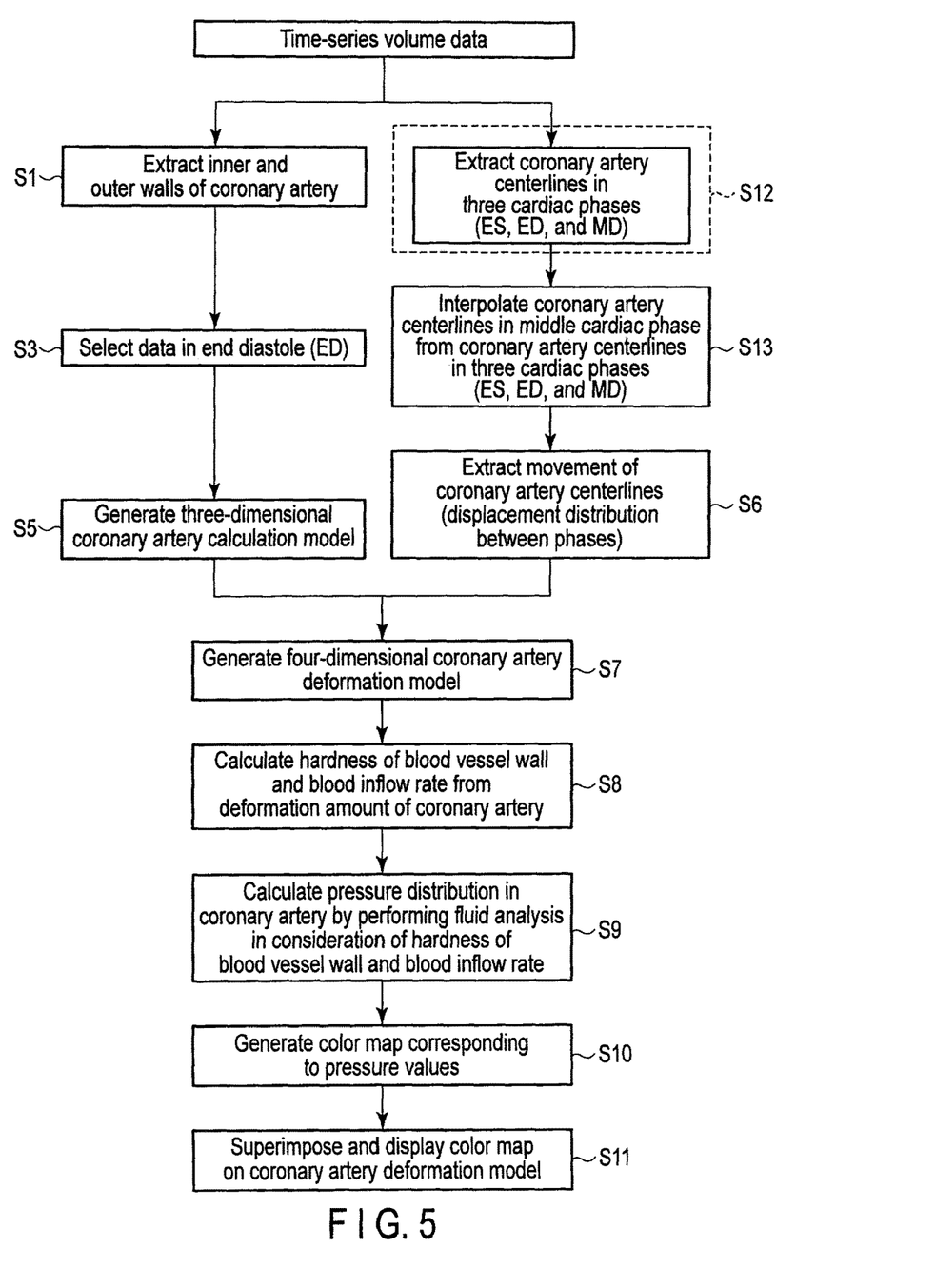
FIG. 5 is a flowchart showing a modification of the procedure in FIG. 2.
Figure 6:
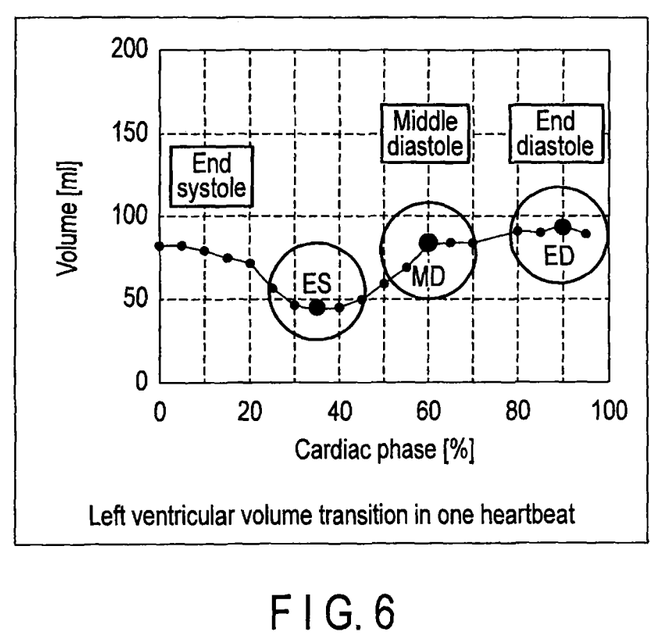
FIG. 6 is a graph showing three cardiac phases (ES, ED, and MD) in step S2 in FIG. 5.

FIG. 5 shows a modification of the procedure in FIG. 2. The same step numbers as in FIG. 2 denote the same steps in FIG. 5, and a description of them will be omitted. In step S12, the centerline analysis processing unit 15 extracts coronary artery centerline structures for volume data selected from the volume data corresponding to the plurality of cardiac phases, stored in the image storage unit 13, under the readout control of the control unit 12, typically volume data corresponding to the end systole (ES) and the end diastole (ED), in which pulsation is relatively small, and the middle phase (MD) between the two cardiac phases, as shown in FIG. 6.

The apparatus generates a plurality of coronary artery centerline structures respectively corresponding to a plurality of cardiac phases between the end systole (ES) and the middle phase (MD) from coronary artery centerline structures in the end systole (ES) and the middle phase (MD) by interpolation processing, and generates a plurality of coronary artery centerline structures respectively corresponding to a plurality of cardiac phases between the end diastole (ED) and the middle phase (MD) from coronary artery centerline structures in the end diastole (ED) and the middle phase (MD) by interpolation processing (S4).

The apparatus can improve interpolation accuracy by interpolating centerline structures in other cardiac phases from the centerline structures in the three cardiac phases. This can improve the accuracy of the four-dimensional coronary artery deformation model and the accuracy of fluid analysis processing as compared with the analysis with two cardiac phases.

Figure 7:
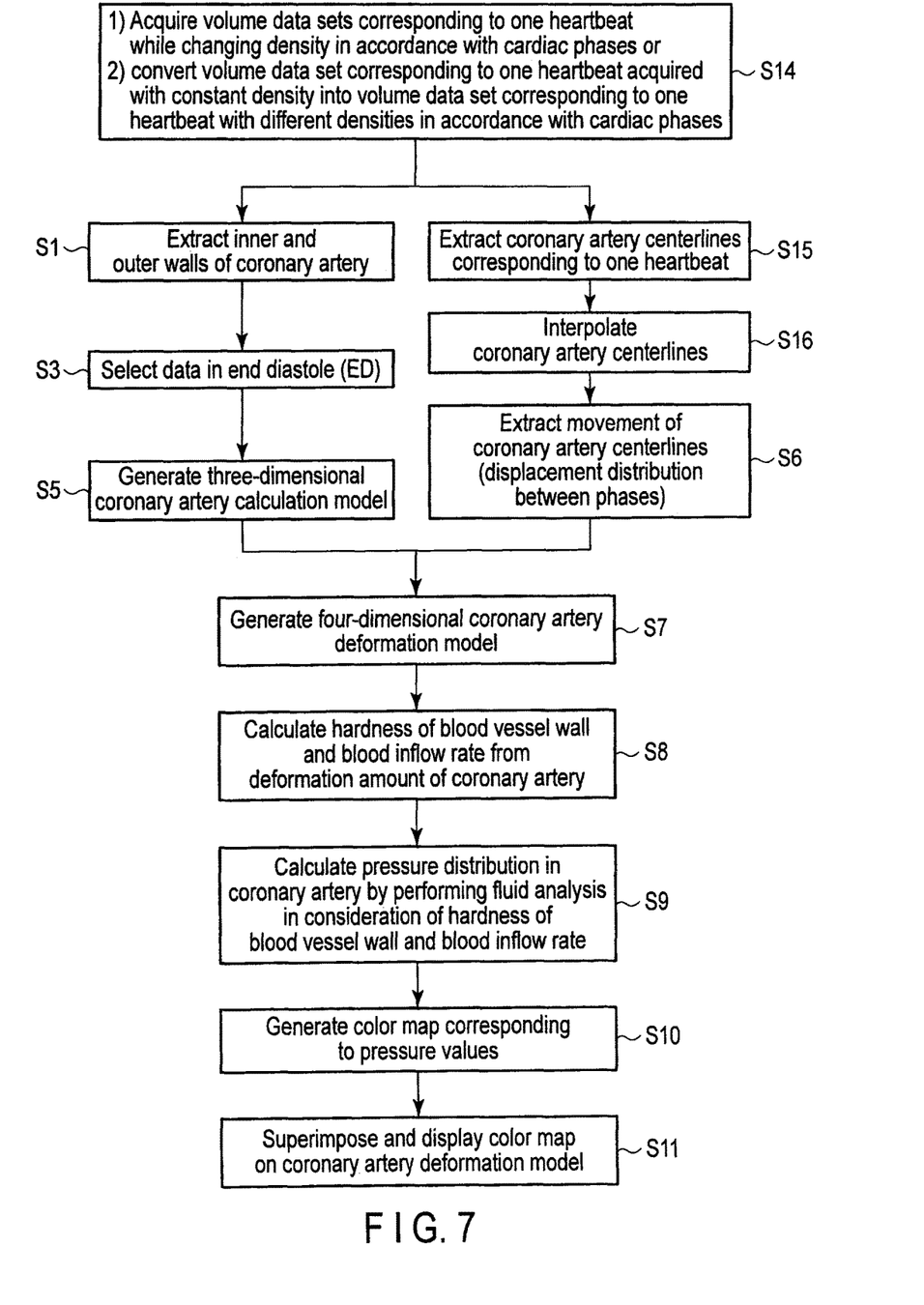
FIG. 7 is a flowchart showing a modification of the procedure in FIG. 2.
Figure 8:
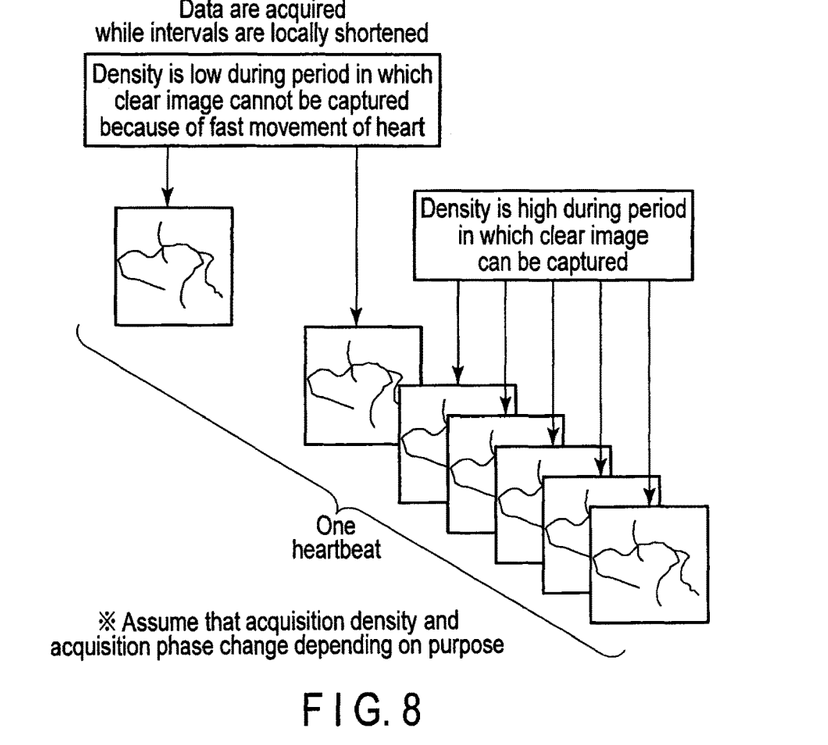
FIG. 8 is a view showing an example of the relationship between heartbeat periods and acquisition densities in step S14 in FIG. 7.

FIG. 7 shows another modification of the procedure in FIG. 2. The same step numbers as in FIG. 2 denote the same steps in FIG. 7, and a description of them will be omitted. In step S14, the apparatus selects volume data to be processed from the volume data respectively corresponding to a plurality of cardiac phases, stored in the image storage unit 13, under the readout control of the control unit 12. The time densities of the volume data selected as data to be processed are irregular, that is, the time intervals between the adjacent volume data are not constant. Typically, the control unit 12 selects volume data with a low density during a period in which a clear image cannot be captured with much blur because of fast movement of the heart. That is, a relatively long time interval is set between the adjacent volume data. In contrast to this, during a period in which a clear image can be captured with less blur because of slow movement of the heart, the apparatus selects volume data with a high density. That is, a relatively short time interval is set between the adjacent volume data.

Note that selecting volume data with irregular densities enables the CT apparatus 2 to change the acquisition density of volume data in accordance with a cardiac phase and change all the volume data acquired and stored in this manner into volume data to be processed.

The apparatus extracts coronary artery centerline structures from the volume data selected with variable densities corresponding to the movement of the heart (S15), and generates, from these coronary artery centerline structures, a plurality of coronary artery centerline structures respectively corresponding to one or a plurality of cardiac phases between them (S16).

This can further improve the interpolation accuracy and reduce the influence of motion artifacts more than by interpolation of centerline structures in other cardiac phases from centerline structures in two or three cardiac phases. This makes it possible to further improve the accuracy of a four-dimensional coronary artery modification model and the accuracy of fluid analysis processing more than the accuracy of analysis with two cardiac phases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising:
   circuitry configured to
   set a plurality of capture timings in one heartbeat of a heart based on cardiac phases, wherein a long time interval is set for a period in which movement of the heart is fast, and a short time interval is selected for a period in which movement of the heart is slow,
   capture plurality of volume data at the plurality of capture timings,
   extract at least two coronary artery centerline structures from the volume data,
   generate a plurality of coronary artery centerline structures concerning other cardiac phases between the at least two specific cardiac phases in the one heartbeat by interpolating the plurality of coronary artery centerline structures based on the at least two extracted coronary artery centerline structures, and
   calculate a plurality of displacement distributions representing a displacement at each point on the coronary artery centerline structure between respective cardiac phases of the plurality of cardiac phases, based on the plurality of coronary artery centerline structures at the phases in the one heartbeat.

2. The medical image processing apparatus according to claim 1, wherein the coronary artery centerline structures concerning the other cardiac phases are interpolated from a coronary artery centerline structure extracted from an image in an end systole phase of the heart and a coronary artery centerline structure extracted from an image in an end diastole phase.

3. The medical image processing apparatus according to claim 1, wherein the coronary artery centerline structures concerning the other cardiac phases are interpolated from a coronary artery centerline structure extracted from an image in an end systole phase of the heart, a coronary artery centerline structure extracted from an image in an end diastole phase, and a coronary artery centerline structure extracted from an image in a middle cardiac phase between the end systole and the end diastole.

4. The medical image processing apparatus according to claim 1, wherein time intervals between adjacent images of the plurality of images are irregular.

5. The medical image processing apparatus according to claim 1, wherein the volume data concerns a region including the heart.

6. A medical image processing apparatus, comprising:
   circuitry configured to set a plurality of capture timings in one heartbeat of a heart based on cardiac phases, wherein a long time interval is set for a period in which movement of the heart is fast, and a short time interval is selected for a period in which movement of the heart is slow, capture plurality of volume data at the plurality of capture timings, extract at least two coronary artery centerline structures from the volume data, generate a plurality of coronary artery centerline structures concerning other cardiac phases between the at least two specific cardiac phases in one heartbeat of the heart by interpolating the plurality of coronary artery centerline structures based on the at least two extracted coronary artery centerline structures, calculate a plurality of displacement distributions representing a displacement at each point on the coronary artery centerline structure between respective cardiac phases of the plurality of cardiac phases, based on the plurality of coronary artery centerline structures at the phases in the one heartbeat, generate a three-dimensional coronary artery reference model from the volume data corresponding to at least one of the two cardiac phases, generate a plurality of three-dimensional coronary artery models for the phases in the one heartbeat by deforming the three-dimensional coronary artery reference model based on the plurality of displacement distributions, and calculate hardness of a blood vessel wall and blood inflow rate of a coronary artery corresponding to each of the plurality of cardiac phases in one heartbeat of the heart from a temporal change in the plurality of three-dimensional coronary artery models.

7. The medical image processing apparatus according to claim 6, wherein the three-dimensional coronary artery reference model is generated from volume data concerning a cardiac phase in an end diastole.

8. The medical image processing apparatus according to claim 6, further comprising a display configured to display the three-dimensional coronary artery model in a cardiac phase in the one heartbeat.

9. The medical image processing apparatus according to claim 6, wherein the plurality of three-dimensional generated coronary artery models constitute time-series data to form a four-dimensional coronary artery deformation model.

10. The medical image processing apparatus according to claim 6, wherein the coronary artery centerline structures concerning the other cardiac phases are interpolated from a coronary artery centerline structure extracted from an image in an end systole phase of the heart and a coronary artery centerline structure extracted from an image in an end diastole phase.

11. The medical image processing apparatus according to claim 6, wherein the coronary artery centerline structures concerning the other cardiac phases are interpolated from a coronary artery centerline structure extracted from an image in an end systole phase of the heart, a coronary artery centerline structure extracted from an image in an end diastole phase, and a coronary artery centerline structure extracted from an image in a middle cardiac phase between the end systole and the end diastole.

12. The medical image processing apparatus according to claim 6, wherein time intervals between adjacent images of the plurality of images are irregular.

13. The medical image processing apparatus according to claim 6, wherein the volume data concerns a region including the heart.

14. The medical image processing apparatus according to claim 6, wherein the circuitry is configured to generate a plurality of pressure distributions respectively corresponding to the plurality of cardiac phases from the calculated hardnesses of the blood vessel wall and the calculated blood inflow rates.

15. The medical image processing apparatus according to claim 14, wherein the circuitry is configured to generate a plurality of color maps with different hues corresponding to pressures from the plurality of pressure distributions.

16. The medical image processing apparatus according to claim 15, further comprising a display configured to superimpose and display the color map on the three-dimensional coronary artery model.

* * * * *